United States Patent [19]

Ruhrnschopf et al.

[11] 4,065,397
[45] Dec. 27, 1977

[54] PLANIGRAPHIC X-RAY APPARATUS FOR THE PREPARATION OF TOMOGRAPHIC IMAGES

[75] Inventors: Ernst-Peter Ruhrnschopf, Erlangen; Gerhard Linke, Erlangen-Frauenaurach, both of Germany

[73] Assignee: Siemens Aktiengesellschaft, Berlin & Munich, Germany

[21] Appl. No.: 751,204

[22] Filed: Dec. 16, 1976

Related U.S. Application Data

[63] Continuation-in-part of Ser. No. 627,466, Oct. 30, 1975, abandoned.

[30] Foreign Application Priority Data

| Dec. 9, 1974 | Germany | 2458225 |
| Aug. 8, 1975 | France | 75.24840 |
| Aug. 12, 1975 | United Kingdom | 33623/75 |

[51] Int. Cl.² .......................................... G03B 41/16
[52] U.S. Cl. .............................. 250/445 T; 364/414; 364/515
[58] Field of Search .......... 250/445 T, 445 R, 439 R, 250/358 R, 359, 360; 235/151.3

[56] References Cited

U.S. PATENT DOCUMENTS

3,778,614 12/1973 Hounsfield ...................... 250/445 T

Primary Examiner—Craig E. Church

Attorney, Agent, or Firm—Hill, Gross, Simpson, Van Santen, Steadman, Chiara & Simpson

[57] ABSTRACT

A planigraphic X-ray apparatus for the preparation of transverse tomographic or planigraphic images of an exposure object, which consists of an X-ray measuring arrangement including an X-ray source generating a polyenergetic X-ray beam penetrating through the exposure object, with a radiation receiver which determines the radiation intensity of the X-radiation as a reference value prior to its ingress into the object, and a further radiation receiver which determines the radiation intensity behind the object in the direction of the radiation as attenuated values, through scanning of the projected X-ray beam at sequential equidistant points, a comparator element which forms a measured magnitude from the two values, as well as a drive arrangement for the measuring arrangement, consisting of a pivot mounting for producing rotational movements of the X-ray measuring arrangement through small equidistant angular amounts about a rotational axis generally coincident with the symmetrical longitudinal axis of the exposure object in an alternating sequence with each respective scan and, a measured value converter for the transformation of the measured values into a tomographic image wherein a function stage applies a proximation function to the results obtained with polyenergetic X-ray energy so as to convert the results to values suitable for processing based on the assumption of monoenergetic radiation.

2 Claims, 3 Drawing Figures

PLANIGRAPHIC X-RAY APPARATUS FOR THE PREPARATION OF TOMOGRAPHIC IMAGES

CROSS REFERENCE TO RELATED APPLICATION

The present application is a continuation-in-part application based on our pending application U.S. Ser. No. 627,466 filed Oct. 30, 1975 now abandoned.

FIELD OF THE INVENTION

The present invention relates to a planigraphic X-ray apparatus for the preparation of planigraphic or tomographic images.

The present invention relates to a planigraphic X-ray apparatus for the preparation of transverse tomographic or planigraphic images of an exposure object, which consists of an X-ray measuring arrangement including an X-ray source generating an X-ray beam penetrating through the exposure object, whose cross-sectional expanse perpendicular to the planigraphic plane is equal to the plane thickness, with a radiation receiver which determines the radiation intensity of the X-radiation as a reference value prior to its ingress into the object, and a further radiation receiver which determines the radiation intensity behind the object in the direction of the radiation as weakened or attenuated values through scanning of the projected X-ray beam at sequential equidistant points, a comparator element which forms a measured magnitude from the two values, as well as a drive arrangement for the measuring arrangement consisting of a pivot mounting for producing rotational movements of the X-ray measuring arrangement through small equidistant angular amounts about a rotational axis generally coincident with the symmetrical longitudinal axis of the exposure object in an alternating sequence with each respective scan and, finally, a measured value converter for the transformation of the measured values into a tomographic image.

DISCUSSION OF THE PRIOR ART

A planigraphic X-ray apparatus of the above-mentioned type has become known from U.S. Pat. No. 2,281,931. The tomographic imaging procedure which is described therein makes use of the knowledge that the totality of the rays emerging from the body which is to be planigraphed, penetrate the body in the direction of the transverse plane from infinitely many sides, determines the tomographic image of the cross-section. Employed thereby is an X-ray measuring arrangement in which an X-ray tube produces a narrow X-ray beam, for example, in the form of a fan, which penetrates the body which is to be X-rayed in the tomographic plane, and wherein a radiation receiver located behind the body, as measured in the direction of the rays, registers the X-ray intensities there encountered. Hereby, the X-ray measuring arrangement is swingable about a rotational axis which generally extends through the symmetrical center of the body. In an alternating sequence with each registration, there is assumed a swinging or tilting movement about a predetermined small angle, until there has been reached a pivot range totaling about 180°. The intensity values which are hereby registered from the different porjecting directions are converted into a tomographic image by means of an optical conversion process.

The disadvantages of this arrangement, above all, consists of in that the X-radiation, in particular due to the generally cylindrical form of most exposure objects, is more extensively weakened or attenuated in the center than in the peripheral areas. However, through also greater density destinctions within the object is the radiation attenuated considerably differently. In order to compensate for the attenuation distinctions between the central and peripheral areas due to the cylindrical form, it is already known from U.S. Pat. No.3,778,614 that in a planigraphic apparatus of the above-mentioned type, the object which is to be X-rayed is to be embedded in a rectangularly-shaped tissue-equivalent shaped body. Independently of the fact that the supporting of the object, in particular when it relates to a human body, is uncomfortable and time-consuming, the arrangement of such a shaped body also signifies an increased technical demand while, nevertheless, failing to provide fully satisfying results. Due to the density distinctions which are prevalent interiorly of the body, the radiation now as previously considered across the entire body cross-section, is attenuated considerably differently. In the employment of a polychromatic X-ray spectrum (Bremsstrahlung), as used as a rule in medical X-ray diagnostic installations, there is obtained therefrom a change in the spectral composition or analysis of the radiation in dependence upon the attenuation. As a result thereof, the obtained linear attenuation coefficient can no longer be unequivocably defined. This, above all, may lead to artifacts in complicated structures, which render image evaluation extremely difficult or even impossible. However, at the very least, the local attenuation coefficients can quantitatively no longer be correctly reproduced.

SUMMARY OF THE INVENTION

Accordingly, it is an object of the present invention to compensate for fluctuation in the representation of local density distinctions occasioned by the different spectral analysis of polychromatic radiation after passage through an inhomogeneous body of varying density. For this purpose, it is inventively proposed to provide a function stage which, from the longarithm of the measured value $y$ defined by X-ray intensity $I_0$ in the ray direction ahead of the exposure object of the ray intensity $I$ behind the exposure object as the quotient, forms a correction factor C pursuant to the proximating function.

$$C = \begin{cases} 1 + y \cdot (y - y_1) \cdot (A_0 + A_1 y) \text{ for } 0 \leq y \leq y_1 \text{ resp.} \\ 1 + (y - y_1) \cdot (B_0 B_1 \cdot y + B_2 \cdot y^2) \text{ for } y_1 \leq y \leq 10 \end{cases}$$

with numerical values, dependent upon a selectable normalized radiation spectrum, of $Y_1$; $A_0$; $A_1$; $B_0$; $B_1$ and $B_2$ which, for example, at an X-ray tube voltage of 100 kV and a normalization spectral line at 51 keV, amount to $Y_1 = 4.45$; $A_0 = -0.035$; $A_1 = 0.0039$; $B_0 = -0.04$; $B_1 = -0.0126$ and $B_2 = 0.00075$, and which transmit the correction factor C to a multiplication stage for the multiplicative influencing of the measured signal. The foregoing is predicated on the concept that always when the radiation passes through a thickening or concentration, or also localized concentrations in the body which is to be X-rayed, a hardening takes place which leads to that the body causes a lower X-ray absorption than in an unchanged spectrum. The result thereof is that in those regions of greater planar or strata thickness or densities, there is present behind the patient a relatively too high dosage. This means, and thereon is based the inventive concept, that the more extensively the radiation is absolutely attenuated, the more massive a spectrum change has taken place. However, the greater the difference between the outlet and the inlet spectrum, the greater is the relative dosage change which is occasioned by the spectral shift. The invention is thus predicated on the recognition that it is possible, in dependence upon the radiation intensity occurring behind the patient, to undertake a correction of the measured value pursuant to the above-described functional interrelationship.

BRIEF DESCRIPTION OF THE DRAWINGS

Further details and advantages may now be ascertained from the following detailed description of an exemplary embodiment of the invention, taken in conjunction with the accompanying drawings; in which.

DETAILED DESCRIPTION

Figure 1:
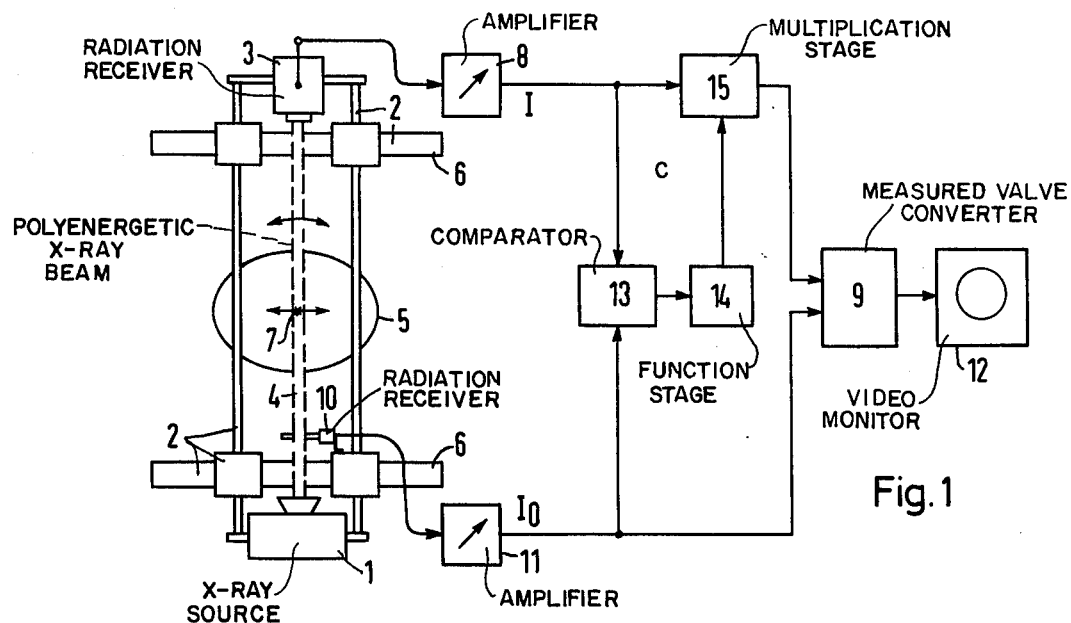
FIG. 1 is a generally schematic representation of a planigraphic X-ray apparatus of the above-mentioned type incorporating a basic circuit for effecting the measured value correction.

According to FIG. 1 of the drawings, an X-ray tube 1 through the intermediary of a mechanical coupling element 2, is connected with a radiation receiver 3 to an X-ray measuring arrangement. The X-ray tube 1 generates a narrow X-ray beam 4 which penetrates through an exposure object 5 and is then measured by the radiation receiver 3. The measuring arrangement 1, 2, 3, for the taking of a tomographic image, is conveyed transversely of the central beam of the X-ray beam 4 on slide rails 6 in a scanning movement in the direction of the plane or stratum across the exposure object 5. After completion of this scan, the measuring arrangement 1, 2, 3 is rotated about a point of rotation 7 which is located approximately in the center of the object 5 through a presently constant amount of up to a few angular degrees. Thereafter is carried out a further scan, and so forth, until the rotational movement has reached an angular magnitude totaling 180°.

The evaluation of the electrical values which are produced by the radiation receiver 3 during the course of this scanning movement with the aid of an amplifier arrangement 8, is carried out with the assitance of a measured value converter 6. In order to be able to reconstruct the distribution of the linear radiation attenuation coefficiencts in the irradiated planar strata, it is also required to form a quotient from between the X-ray intensity $I_0$ which is present preceding the incident radiation and the radiation intensities I occurring behind the object 5 in the direction of the radiation. For this purpose, there is provided a further radiation receiver 10 which, with the aid of an amplifier circuit 11, similarly converts the measured input radiation intensity into corresponding electrical values and transmits them to the measured value converter 9, which forms the quotients from the two signals as digital measured values. These are then processed into a tomographic image by means of mathematical means, such as are generally described in the "Journal of Applied Physics" Volume 34, No. 9, pages 2722 et seq.; and Volume 35, No. 10, pages 2908 et seq.; by A. M. Cormack, under the title "Representation of a Function by its Line Intervals, with some Radiological Applications", which, for example, may then be reproduced on a video monitor 12.

As a prerequisite for the there indicatd calculating method, it is assumed that the incident X-radiation is monochromatic. In practical operation such as radiation is, however, difficult to realize, and one is obligated to be able to operate with a polychromatic (Bremsstrahlenspectrum), which can be taken out of a commercially available X-ray tube. The utilization of such a Bremsstrahlenspectrum does, however, have the result that the spectral composition or analysis varies in dependence upon the X-ray attenuation. The spectrum, in the instance of strong attenuation, is hardened in comparison with its original composition. A harder radiation does, however, have a greater penetrability than a soft radiation, so that measuring errors occur which are dependent upon the spatial density distribution, and which lead to errors in the image representation. Hereby, this can relate to a smudging of present structures, but may also relate to complete falsification or erroneous representations through artifacts.

Figure 2:
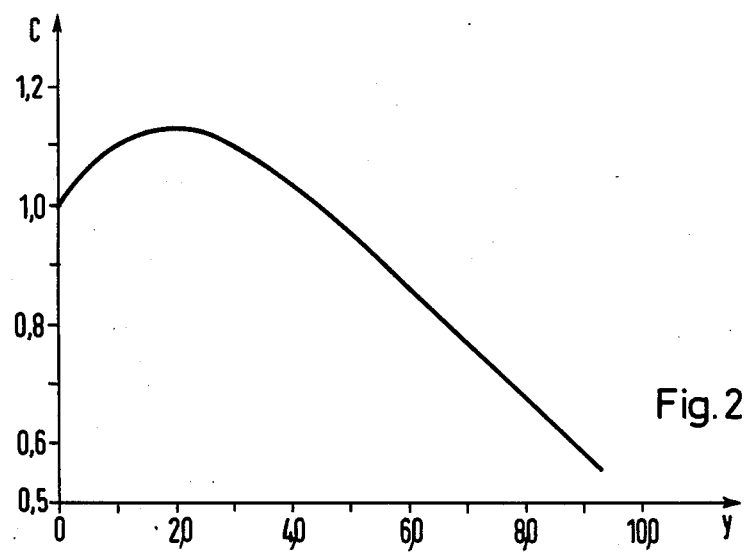
FIG. 2 is a curve plot of the correction function.

Illustrated in FIG. 2 of the drawings, in the form of a curve, is the correction favor C in dependence upon the logarithmic value $y = \log. I_0/I$ relative to a 1.0 normalized reference value, which corresponds to a monochromatic radiation of 51 keV. This curve bases itself on the energy spectrum of radiation withdrawn from a normal X-ray tube at a voltage of 100 kV.

In order to reach the desired correction, in accordance with FIG. 1 the signals $I_0$ and, respectively, I produced by the radiation receivers 3, 8 and 10, 11, are now logarithmated, subtracted in a circuit arrangement 13, and then transmitted to a function stage 14 which, on the basis of the curve shown in FIG. 2 pursuant to the proximating function $$C = \begin{cases} 1 + y \cdot (y - y_1) \cdot (A_0 + A_1 y) \text{ for } 0 \leq y \leq y_1 \text{ resp.} \\ 1 + (y - y_1) \cdot (B_0 B_1 \cdot y + B_2 \cdot y^2) \text{ for } y_1 \leq y \leq 10 \end{cases}$$

calculates a correction value C in the form of a factor for each value $y = \log. I_0/I$ being received, which is conducted to a multiplication stage 15 arranged in the signal path of the signal I, and which corrects the signal I in the desired manner. Due to the quotient formation, this correction can also be undertaken in the signal path of the signal $I_0$, but in the reciprocal form 1/C in lieu of C.

Figure 3:
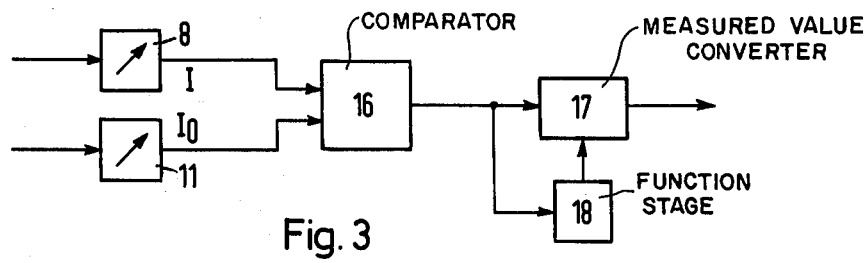
FIG. 3 is a modification of the basic representation of the apparatus according to FIG. 1.

Naturally it is also possible, as shown in FIG. 3, that in lieu of the correction circuit selected in FIG. 1, there is formed from the two signals $I_0$ and I the measured value as the logarithmic quotient from $I_0$ and I with the aid of a circuit arrangement 16 and to transmit this to the measured value converter 17. A function stage 18 is associated with this measured value converter, which has the uncorrected logarithmic measured values transmitted thereto, and on the basis of a correction function, which may be obtained through a mathematical transformation from that represented in FIG. 2, there are determined corresponding correction factors C', and which are transmitted to the measured values converter 17 for the correction of the measured values.

Discussion of FIG. 2

The constants $A_0$, $A_1$, $B_0$, $B_1$ and $B_2$ are determined empirically for the foregoing proximating function so that the two branches of the function C in FIG. 2 lying on opposite sides of the coordinate $y = y_1$, intersect smoothly and without discontinuity at the point $y_1$, as shown in FIG. 2. As seen in FIG. 2 the curve C first rises above the value of 1.0, and after reaching a maximum the curve drops again and passes through 1.0 on its downward trend. The location on the dropping portion curve at which C is again 1.0, is denoted by $y_1$. In accordance with FIG. 2, therefore, $y_1$ is approximately 4.4.

FIG. 2 shows furthermore, that the branch of the curve between $o \leq y \leq y_1$ on one side of $y_1$, intersects smoothly the branch $y_1 \leq y \leq 10$ on the other side of $y_1$. The two branches intersect at $y_1$ without discontinuity. The constants noted above are selected so as to obtain the smooth continuous intersection of the two branches as shown in FIG. 2.

For the sake of a more concrete explanation of the approximating function, the following Table A will illustrate the computation of the value C for values of $y$ of 0, 1, 2, 3, 4 and 4.45 where as previously given in the Summary of the Invention, $y_1 = 4.45$; $A_0 = -0.035$; and $A_1 = 0.0039$. Similarly, the following Table B shows the values of the proximating function for values of $y$ of 4.45, 5, 6, 7, 8 and 9, where $B_0 = -0.04$; $B_1 = -0.0126$ and $B_2 = 0.00075$.

TABLE A

| $y$ | $(y-y_1)$ | $(A_o + A_1 y)$ | $1 +(y) \cdot (y - y_1) \cdot (A_o + A_1 y)$ |
| --- | --- | --- | --- |
| 0 | −4.45 | | $1 +(0) \cdot (-4.45) \cdot ( \quad ) = 1.00$ |
| 1 | −3.45 | −.0311 | $1 +(1) \cdot (-3.45) \cdot (-.0311) = 1.11$ |
| 2 | −2.45 | −.0272 | $1 +(2) \cdot (-2.45) \cdot (-.0272) = 1.13$ |
| 3 | −1.45 | −.0233 | $1 +(3) \cdot (-1.45) \cdot (-.0233) = 1.10$ |
| 4 | −.45 | −.0194 | $1 +(4) \cdot (-.45) \cdot (-.0194) = 1.03$ |
| 4.45 | 0 | | $1 + (4.45) \cdot (0) \cdot ( \quad ) = 1.00$ |

TABLE B

| $y$ | $y - y_1$ | $(B_0 + B_1 \cdot y + B_2 \cdot y^2)$ | $1 + (y - y_1) \cdot (B_o + B_1 \cdot y + B_2 \cdot y^2)$ |
| --- | --- | --- | --- |
| 4.45 | 0 | | $1+(0) \quad \cdot ( \quad )=1.00$ |
| 5 | .55 | −.0843 | $1+(.55) \cdot (-.0843) = .95$ |
| 6 | 1.55 | −.0886 | $1+(1.55) \cdot (-.0886) = .86$ |
| 7 | 2.55 | −.09145 | $1+(2.55) \cdot (-.09145) = .77$ |
| 8 | 3.55 | −.0928 | $1+(3.55) \cdot (-.0928) = .67$ |
| 9 | 4.55 | −.09265 | $1+(4.55) \cdot (-09265) = .58$ |

From a qualitative standpoint, it will be seen that $y$ values between 0 and 2.0 represent objects having a relative low attenuation for X-ray energy of a given intensity, for example X-ray energy at an intensity of 51keV. Thus, in this range of attenuation values, as the output from comparator 13 increases between 0 and 2.0, the measured X-ray spectrum is relatively greatly attenuated in comparison to a reference spectrum at 51keV, so that it is necessary to multiply the output of amplifier 8 in FIG. 1 by progressively increasing values of C in this range, such that the output of multiplier 15, FIG. 1, gives corrected values of transmitted radiation which are properly proportional to the transmitted radiation which would be measured for a spectral line at 51keV. Thus, at these low levels of attenuation, the attenuation of the normal X-ray spectrum below 51keV is so marked that the total energy transmitted is markedly too low, reaching a peak in this sense for a $y$ value of 2.0. In the range from $y$ values of 2.0 to 4.45, the overall attenuation of the X-ray spectrum still exceeds that for a spectral line of 51 keV, but the difference is becoming progressively less marked, until at the $y$ value of 4.45, the attenuation of the total X-ray spectrum is in conformity with that for a spectral line of 51keV. Beyond a $y$ value of 4.45, the normal X-ray spectrum is being progressively hardened such that the total transmitted energy exceeds that for a spectral line at 51keV, and the differential is becoming more marked as the $y$ value increases between 4.45 and a value such as $y = 9$, for example. Thus, in the range of $y$ values from comparator 13 above the value 4.45, function stage 14 will provide C factors which are progressively less than 1, so that the output of amplifier 8 will be progressively reduced by means of multiplier 15 to compensate for the progressive hardening of the X-ray spectrum.

Accordingly, pursuant to the teachings of the present invention, a comparator such as 13 or 16 forms a measured magnitude (such as $y$) from the reference value ($I_O$) and the attenuated value(I). A function stage such as 14 or 18 is provided for forming from the measured value ($y$) which is defined as a function of the quotient of the X-ray intensity $I_O$ in the ray direction proceeding the exposure object and the X-ray intensity I behind the exposure object, a correction factor (such as C or C') pursuant to a proximating function which serves to normalize the output of the measured value converter (such as 9 or 17) so as to essentially conform to values which would be obtained for monoenergetic X-ray energy of a given energy level (such as the example of 51keV), the proximating function corresponding to a curve (such as shown in FIG. 2) extending substantially through points $y = 0$, C = 1.0 (FIG. 2); $y = y_1$, C = 1.0 (Table A for the case $y_1 = 4.45$); and which reaches a peak value of C intermediate $y = 0$ and $y = y_1$ (FIG. 2), and which progressively decreases in value of C as a function of $y$ for values of $y$ between $y = y_1$ and $y = 10$ (Table B and FIG. 2).

Accordingly, with the use of a function stage as disclosed herein such as the function stage 14 of FIG. 1 or the function stage 18 of FIG. 3, the measured values at the output of multiplication stage 15 or the corresponding values at the output of measured value converter 17 will essentially conform to those which would be obtained with monoenergetic X-ray energy at the normalization energy level (such as 51 keV). In this way, the tomographic image may be processed by means of the mathematical procedures referred to herein while minimizing any error because of the necessity of actually operating with a polyenergetic X-ray spectrum.

While there has been shown what is considered to be the preferred embodiment of the invention, it will be obvious that modifications may be made which come within the scope of the disclosure of the specification.

What is claimed is:

1. In a planigraphic X-ray apparatus for the preparation of tomographic images of an exposure object; including an X-ray measuring arrangement having an X-ray source generating an X-ray beam penetrating the exposure object, the cross-sectional expanse of said beam perpendicular to the planigraphic plane being equal to the plane thickness; a first radiation receiver for determining the radiation intensity of the X-radiation as a reference value preceding its ingress into the object; a second radiation receiver for determining the radiation intensity behind the object in the direction of the radiation as attenuated values through scanning of the projected X-ray beam at sequential equidistant points; a comparator for forming a measured magnitude from the reference and attenuated values; a drive means for the measuring arrangement including a pivot mounting for producing rotational movement of the X-ray measuring arrangement through small equidistant angular amounts about a rotational axis generally coincident with the symmetrical longitudinal axis of the exposure object in alternating sequence with respectively each scan; and a measured value converter for transforming the measured values into a tomographic image the improvement comprising: a function stage for forming, from the logarithm of the measured value $y$ defined by the X-ray intensity $I_0$ in the ray direction preceding the exposure object and the X-ray intensity $I$ behind the exposure object as the quotient, a correction factor C pursuant to the proximating function $$C = \begin{cases} 1 + y \cdot (y - y_1) \cdot (A_0 + A_1 y) \text{ for } 0 \leq y \leq y_1 \text{ resp.} \\ 1 + (y - y_1) \cdot (B_0 B_1 \cdot y + B_2 \cdot y^2) \text{ for } y_1 \leq y \leq 10 \end{cases}$$

with counting values, dependent upon a selectable normalized radiation spectrum, of $y_1$, $A_0$; $B_0$; and $B_2$, said and counting values, at an X-ray tube voltage of 100 kV and a normalization spectral line at 51 keV, are $y_1 = 4.45$; $A_0 = -0.035$; $A_1 = 0.0039$; $B_0 = -0.04$; $B_1 = -0.0126$; and $B_2 = 0.00075$; and a multiplication stage receiving said correction factor C for the multiplicative influencing of the measured value.

2. In a planigraphic X-ray apparatus for the preparation of tomographic images of an exposure object; including an X-ray measuring arrangement having an X-ray source generating an X-ray beam penetrating the exposure object, the cross-sectional expanse of said beam perpendicular to the planigraphic plane being generally equal to the plane thickness; a first radiation receiver for determining the radiation intensity of the X-radiation as a reference value preceding its ingress into the object; a second radiation receiver for determining the radiation intensity behind the object in the direction of the radiation as attenuated values through scanning of the projected X-ray beam at sequential equidistant points; a comparator for forming a measured magnitude from the reference and attenuated values; a drive means for the measuring arrangement including a pivot mounting for producing rotational movement of the X-ray measuring arrangement through small equidistant angular amounts of a rotational axis generally coincident with the symmetrical longitudinal axis of the exposure object in alternating sequence with respectively each scan; and a measured value converter for transforming the measured values into a tomographic image, the improvement comprising: a function stage for forming, from the measured value $y$ defined as a function of the quotient of the X-ray intensity $I_0$ in the ray direction preceding the exposure object and the X-ray intensity I behind the exposure object, a correction factor C pursuant to a proximating function which serves to normalize the output of the measured value converter so as to essentially conform the values which would be obtained for monoenergetic X-ray energy level, said proximating function corresponding to a curve extending substantially through points $y = 0$, $C = 1.0$; $y = y_1$, $C = 1.0$; and which reaches a peak value of C intermediate $y = O$ and $y = y_1$, and which progressively decreases in value of C as a function of $y$ for values of $y$ between $y = y_1$ and $y = 10$, said function stage forming a multiplicative correction factor C for correction of the measured values, the correction factor C corresponding to a proximating function such that C is equal to one at $y$ equal zero and at $y$ equals about 4.45, and such that the value of C corresponds to a curve which progressively increses and substantially passes through the coordinates $y = 0$, $C = 1.0$; $y = 1.0$, $C = 1.11$; $y = 2.0$, $C = 1.13$, between $y = 0$ and $y = 2.0$; and progressively decreases and substantially corresponds to a curve through points having the proximate coordinates $y = 3.0$, $C = 1.10$; $y = 4.0$, $C = 1.03$, $y = 5.0$, $C = 0.95$; $y = 6.0$; $C = 0.86$; $y = 7.0$, $C = 0.77$; $y = 8.0$, $C = 0.67$; and $y = 9.0$, $C = 0.58$, between $y = 2.0$ and $y = 9.0$.

* * * * *